(12) United States Patent
van Deursen et al.

(10) Patent No.: US 7,097,812 B2
(45) Date of Patent: Aug. 29, 2006

(54) DEVICE FOR STORING AND/OR TREATING CHEMICALS

(75) Inventors: Johannes Martinus Petrus van Deursen, Middelburg (NL); Marinus Frans Van der Maas, Arnemuiden (NL)

(73) Assignees: SGT Exploitatie B.V., Middelburg (NL); Joint Analytical Systems GmbH, Moers (DE)

( * ) Notice: Subject to any disclaimer, the term of this patent is extended or adjusted under 35 U.S.C. 154(b) by 0 days.

(21) Appl. No.: 10/803,647

(22) Filed: Mar. 18, 2004

(65) Prior Publication Data

US 2004/0173508 A1   Sep. 9, 2004

Related U.S. Application Data

(63) Continuation of application No. 10/244,788, filed on Sep. 16, 2002, now Pat. No. 6,733,731, which is a continuation of application No. 09/067,483, filed on Apr. 27, 1998, now Pat. No. 6,475,443.

(30) Foreign Application Priority Data

Apr. 28, 1997   (NL)   .................... 1005914

(51) Int. Cl.
*B01L 3/00*   (2006.01)

(52) U.S. Cl. ................ 422/102; 210/198.2; 340/572.1; 340/572.8; 422/59; 422/60; 422/69; 422/70; 700/231

(58) Field of Classification Search .............. 210/198.2; 340/572, 572.1, 572.8, 825.24; 422/59–60, 422/69–70, 102; 700/231
See application file for complete search history.

(56) References Cited

U.S. PATENT DOCUMENTS

| 4,154,690 A | 5/1979 | Ballies ........................ 210/516 |
| 4,572,067 A | 2/1986 | Fischer |
| 4,857,893 A | 8/1989 | Carroll ........................ 340/572 |
| 5,008,661 A | 4/1991 | Raj ........................ 340/825.54 |
| 5,121,748 A | 6/1992 | Ditz et al. ................... 128/631 |
| 5,211,129 A | 5/1993 | Taylor et al. ................... 119/3 |
| 5,252,962 A | 10/1993 | Urbas et al. ........... 340/870.17 |
| 5,566,441 A | 10/1996 | Marsh et al. ................. 29/600 |
| 5,574,230 A | 11/1996 | Baugh |
| 5,632,168 A | 5/1997 | Yano ........................... 70/278 |
| 5,880,675 A | 3/1999 | Trautner ..................... 340/572 |
| 5,889,197 A * | 3/1999 | van der Maas et al. ... 73/23.42 |
| 5,892,458 A * | 4/1999 | Anderer et al. .......... 340/10.41 |
| 5,930,145 A * | 7/1999 | Yuyama et al. ............. 700/231 |
| 5,961,923 A * | 10/1999 | Nova et al. ................ 422/68.1 |
| 6,100,026 A | 8/2000 | Nova et al. .................... 435/6 |
| 6,446,515 B1 * | 9/2002 | Cole et al. ............... 73/863.21 |
| 6,475,443 B1 * | 11/2002 | van Deursen et al. ...... 422/102 |
| 6,733,731 B1 * | 5/2004 | van Deursen et al. ...... 422/102 |

FOREIGN PATENT DOCUMENTS

| DE | 2 508 201 | 9/1976 |
| DE | 43 01 401 A1 | 7/1994 |
| DE | G 94 16 270.0 | 12/1994 |
| DE | 19518936 | 12/1995 |

(Continued)

*Primary Examiner*—Arlen Soderquist
(74) *Attorney, Agent, or Firm*—Weingarten, Schurgin, Gagnebin & Lebovici LLP

(57) ABSTRACT

A device for storing and/or treating chemicals is described. The device includes a glass casing provided with a receiving cavity for storing chemicals therein, and further includes a transponder having a memory, the transponder being arranged in the device such that it cannot be affected by the chemicals.

16 Claims, 5 Drawing Sheets

FOREIGN PATENT DOCUMENTS

| | | |
|---|---|---|
| DE | 4439914 | 5/1996 |
| EP | 619246 | 10/1994 |
| EP | 0 635 305 A1 | 1/1995 |
| EP | 0 637 750 A2 | 2/1995 |
| EP | 706825 | 4/1996 |
| FR | 2 555 744 A | 5/1985 |
| JP | 2-215465 | 8/1990 |
| WO | 89/08264 | 9/1989 |

* cited by examiner

DEVICE FOR STORING AND/OR TREATING CHEMICALS

This application is a continuation of U.S. patent application Ser. No. 10/244,788 filed Sep. 16, 2002 entitled DEVICE FOR STORING AND/OR TREATING CHEMICALS now U.S. Pat. No. 6,733,731 issued May 11, 2004, which is a continuation of U.S. patent application Ser. No. 09/067,483 filed Apr. 27, 1998 entitled DEVICE FOR STORING AND/OR TREATING CHEMICALS now U.S. Pat. No. 6,475,443 issued Nov. 5, 2002. This application claims the priority of Dutch Patent Application No. 1005914 filed Apr. 29, 1997, which is incorporated herein by reference.

FIELD OF THE INVENTION

The present invention relates to a device for storing and/or treating chemicals, comprising a casing which is made of glass and is provided with a receiving cavity for storing chemicals therein.

BACKGROUND OF THE INVENTION

Devices for storing and/or treating chemicals are utilized in bulk quantities by the chemical industry, research laboratories, medical laboratories and like institutes. The known devices include, for instance, sampling tubes as described in Dutch patent application NL-A-1003492, a sample bottle or vial, a test tube or blood tube, a Petri dish, and HPLC column, or like devices comprising a glass casing provided with a receiving cavity for storing chemicals therein.

Often, it is a problem to record what is stored in a known device and under what conditions storage occurred. Thus, it happens regularly in hospitals that tubes of blood are mixed up and so the results of the blood test are linked with the wrong patient. With sampling tubes that are used specifically for taking samples from gases, such as, for instance, the atmosphere, it is necessary to record under what conditions the samples were taken. Pressure, temperature, air humidity and like data are of direct influence on the concentrations of the samples that are taken. Since these sampling activities often take place in the absence of attendant personnel, there is no opportunity of registering this kind of data, so that other solutions to resolve these problems have been realized. In sampling the atmosphere, sometimes use is made of a special pump which keeps the pressure, temperature, and humidity of the air which is passed through the sampling tube at a constant value. Such a pump is particularly costly and would not be necessary if the data of the atmospheric pressure, the air humidity, the temperature and the like were known. In other absorption processes, too, such data play an important role. In the case of, for instance, a high performance liquid chromatography (HPLC) column, keeping record of the measurements performed is a labor-intensive job which can easily lead to errors.

SUMMARY OF THE INVENTION

The object of the invention is to provide a device of the type defined in the opening paragraph hereof, without the above-mentioned drawbacks. To that end, according to the invention, the device is characterized in that it comprises a transponder including a memory, the transponder being arranged in the device such that it cannot be affected by the chemicals. The transponder can be designed in a variety of ways. Thus, it can be provided with a memory in which only a fixed number is stored. The data to be stored in relation to the chemicals received in a given device are stored in a central computer with reference to the identification number stored in the transponder.

Such a solution is practical in particular when the location where the chemicals are received in the receiving cavity of the casing of the device is in the proximity of the central computer in which the data of interest are stored. There are many applications, however, where measurement occurs remote from a central computer and hence no freely available memory for storing these data is present. In that case, according to a further elaboration of the invention, it is particularly favorable when the transponder is provided with programmable memory. In that case, data observed in situ can be stored in the memory of the transponder and read out by a central computer at a later time. Optionally, the transponder can contain control data on the basis of which processing apparatus can be driven.

According to a further elaboration of the invention, the transponder is melted-in in a closed glass housing which constitutes an inseparable part of the device. Owing to the presence of the glass housing, such a transponder cannot be contaminated or destroyed by the chemicals received in the receiving cavity of the device.

Further elaborations of the invention are described in the subclaims and will hereinafter be further clarified with reference to the drawing, on the basis of a number of exemplary embodiments.

BRIEF DESCRIPTION OF THE DRAWINGS

FIG. 4 shows a cross-sectional view of a test tube according to a second embodiment;

DETAILED DESCRIPTION OF THE INVENTION

Figure 1:
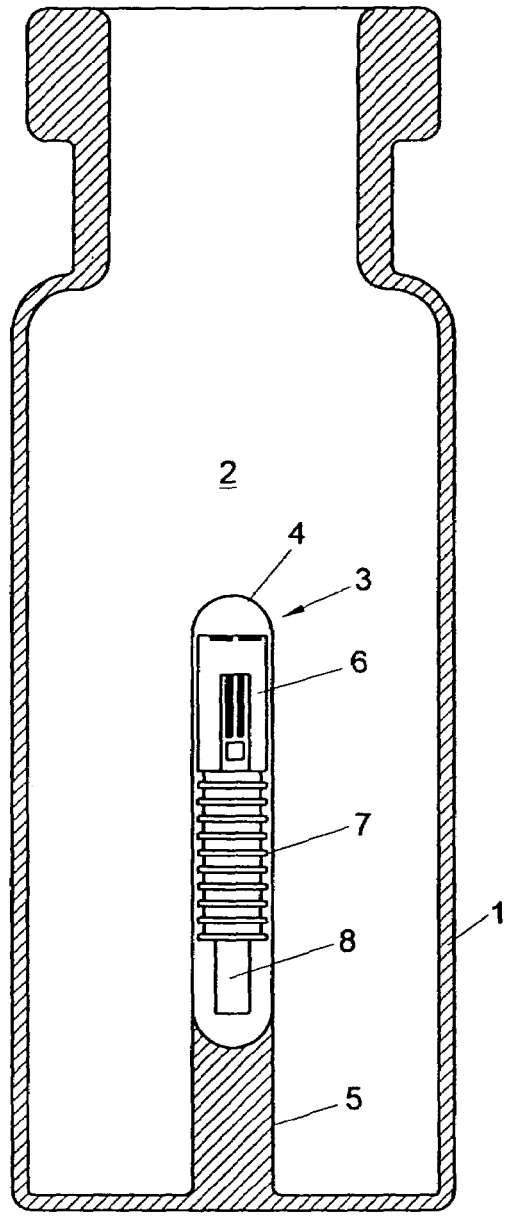
FIG. 1 shows a cross-sectional view of a first exemplary embodiment of a sample vial.

The exemplary embodiment of a sampling vial shown in FIG. 1 comprises a casing 1 made of glass. The casing 1 comprises a receiving cavity 2 for receiving chemicals therein. The vial further comprises a transponder 3. The transponder is melted-in in a closed glass housing 4. The glass housing 4 is inseparably connected to the device through a fastening column 5. The closed glass housing 4 is fused onto the fastening column 5. The transponder 3 accommodated in the glass housing comprises a chip 6 and an antenna 7. In the subject case, the antenna is designed as a coil-shaped element. The coil-shaped element is wound around a rod 8 of conducting material to enhance the antenna function. The chip 6 contains a memory. In the present exemplary embodiment and in all exemplary embodiments of the transponder 3 to be discussed hereinafter, the transponder can contain a so-called resonant circuit. The transponder can be of the transmission type and hence actively transmit signals in return, or of the adsorption type, whereby, as a result of the presence of an internal resistance, which is optionally variable, also a message can be issued. Such a resonant circuit is generally provided with a coil and a capacitance.

Figure 2:
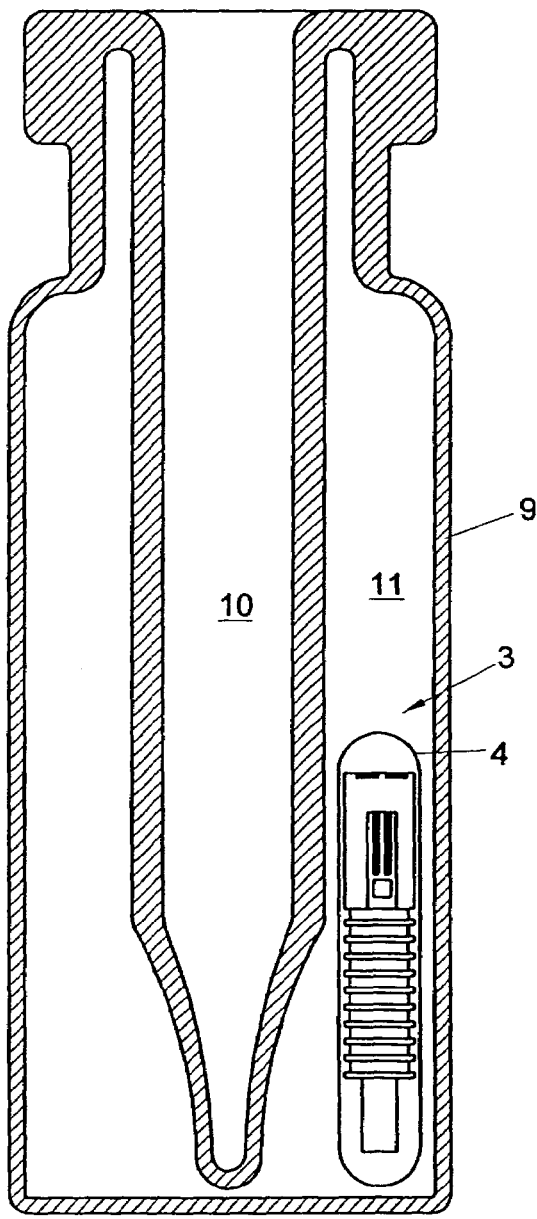
FIG. 2 shows a similar cross-sectional view of a second exemplary embodiment of a sample vial.

The exemplary embodiment of a sample vial represented in FIG. 2 likewise comprises a casing 9 of glass, including a receiving cavity 10. The receiving cavity 10 is intended for receiving chemicals therein. The casing 9 additionally comprises a closed receiving cavity 11 accommodating a transponder 3 in a glass housing 4. The transponder 3 is of the same type as represented in FIG. 1 and is loosely received in the cavity 11. Since the cavity 11 is a closed space, the transponder 3 constitutes an inseparable part of the device.

Figure 3:
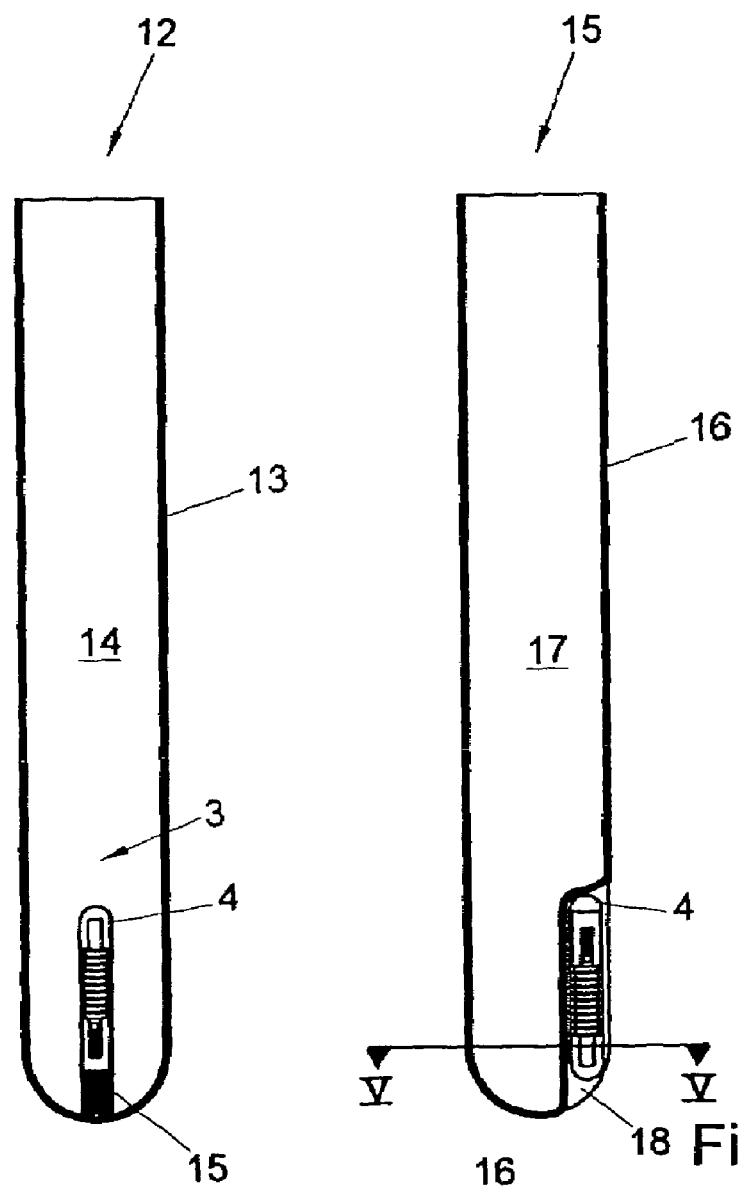
FIG. 3 shows a cross-sectional view of a test tube according to a first embodiment.

FIG. 3 shows a test tube or blood tube 12 which is provided with a transponder 3. The test tube comprises a casing 13 made of glass, and a receiving cavity 14. Provided in the receiving cavity 14 is a fastening column 15 by which the transponder 3, via the glass housing 4, is fixedly connected to the casing 13.

FIG. 4 shows an alternative exemplary embodiment of a test tube 15, likewise comprising a glass casing 16 and a receiving cavity 17. Provided in the sidewall of the casing 16 is a recess 18 in which the transponder 3 accommodated in a glass housing 4 is received with a proper fit. Optionally, attachment can be ensured by some kit, or the two housings 16 and 4 can be connected to each other in that they are fused onto each other.

Figure 5:
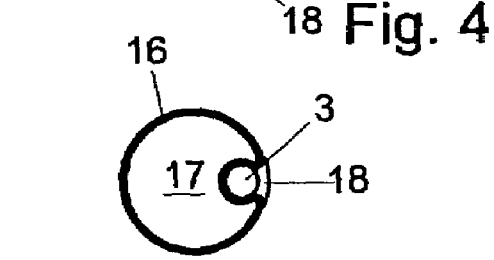
FIG. 5 shows a section taken on line V—V in FIG. 4.

FIG. 5 shows the cross-sectional view taken along line V—V in FIG. 4. FIG. 5 clearly shows in what way the recess 18 is provided in the wall of the glass casing 16.

Figure 6:
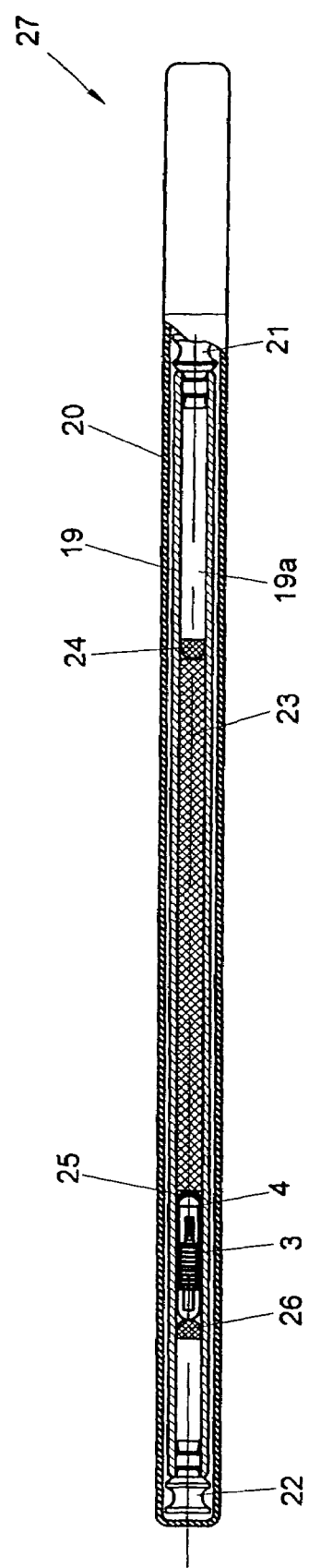
FIG. 6 shows a cross-sectional view of a sampling tube according to a first exemplary embodiment.

FIG. 6 shows an exemplary embodiment of a sampling tube 19. In the exemplary embodiment shown, the sampling tube is received in a package 20 which is made of glass. The sampling tube 19 is closed at both ends with a Teflon cap 21, 22. Further, in a receiving cavity 19a of the sampling tube 19 made of glass, absorption material 23 is received, confined between two sieves 24, 25. Disposed on the left of the left-hand sieve 25 is a transponder 3 which is accommodated in a glass housing 4. The transponder 3 is fixed in this position by a third sieve 26 made of metal. Preferably, the transponder 3 can resist a high temperature for some time, so that the absorption material can be regenerated and the sampling tube can be reused. The packaging tube 20 is closed at the end 27, for instance in that it is melted up. Preferably, the packaging tube 20 is filled with inert gas, so that the absorption material 23 is not contaminated. If the packaging tube 20 were absent, the absorption material 23, in the course of time, would be subject to contamination by air entering through the Teflon caps 21, 22.

Figure 7:
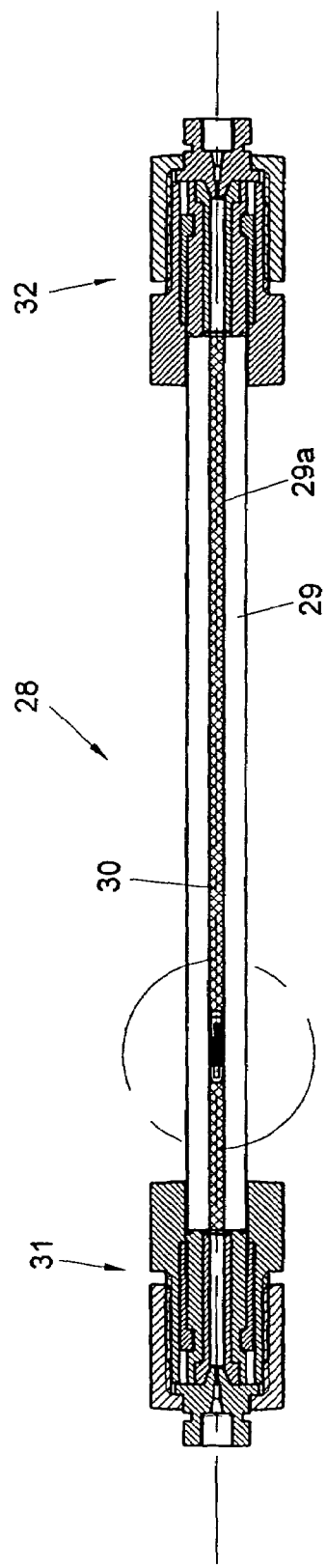
FIG. 7 shows a cross-sectional view of an HPLC column according to a first embodiment.
Figure 8:
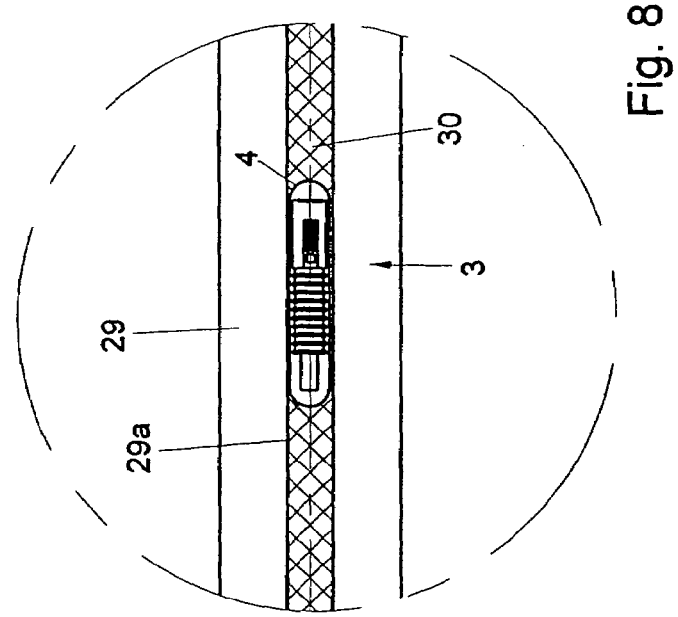
FIG. 8 shows a detail of the HPLC column represented in FIG. 7.

FIG. 7 shows a cross-sectional view of an HPLC (high performance liquid chromatography) column. Such a column 28 comprises a casing 29 made of glass. The glass casing 29 includes a receiving cavity 29a which is at least partly filled with separation material 30. The ends of the glass casing 29 are provided with coupling elements 31, 32, by means of which the HPLC column can be installed in a chromatograph. In the present exemplary embodiment, the transponder 3, disposed in a glass housing 4, is embedded in the separation material 30. Although the drawing figure suggests that the transponder 3 completely closes off the channel 29a in which the separation material 30 is disposed, this is not the case. The separation material 30 has very small pores, so that the carrier liquid must be forced through the separation material 30 at a very high pressure. The clearance between the inner walls of the glass casing 29 and the circumferential wall of the glass housing 4 of the transponder 3 is particularly large in proportion to the pore size, so that the transponder 3 hardly constitutes a constriction in the channel 29a of the column 28. Optionally, the channel 29a in which the separation material 30 is disposed can be provided with a slightly greater diameter.

Figure 9:
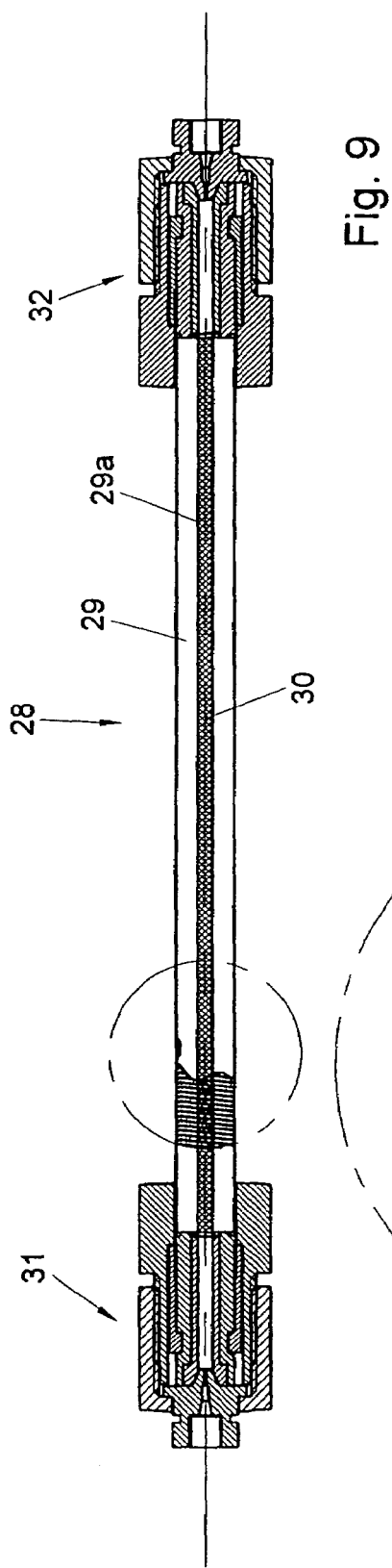
FIG. 9 shows a cross-sectional view of a second embodiment of an HPLC column.
Figure 10:
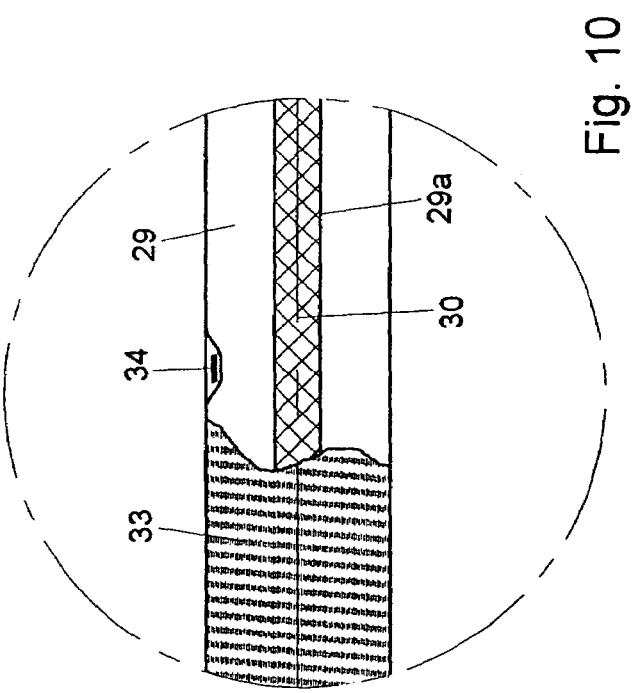
FIG. 10 shows a detail of the HPLC column represented in FIG. 9.

FIGS. 9 and 10 show an alternative design of an HPLC column 28 according to the invention, in which use is made of a different type of transponder. A track 33 of conductive material has been applied in a spiral configuration to the external circumferential surface of the glass casing 29 by a vapor deposition technique. Vapor deposition of metal ions on glass is a technique known per se. The spiral track 33 of conductive material is connected to a transponder chip 34 embedded in the casing 29 made of glass.

It is noted that the invention is not limited to the exemplary embodiments described, but that various modifications are possible within the scope of the invention. Thus, for instance, a Petri dish could equally be fitted with a transponder. Basically any glassware intended for storing and/or treating chemicals, where the recordal of data regarding those chemicals is essential, is eligible for incorporation of a transponder. To date, the transponders, which are known per se, have been used solely for identifying animals or recording data in a chip card and the like. The idea of utilizing these transponders in glassware which is generally utilized as being disposable yields an entirely new range of possibilities, which can lead to enormous savings during use of the glassware.

The invention claimed is:

1. A device for storing and/or treating chemicals, comprising:
   a casing in the form of a sampling tube having two open ends, the sampling tube defining a receiving cavity for storing chemicals therein, the receiving cavity accommodating an absorption material,
   wherein the sampling tube is provided with a transponder including a memory, the transponder being arranged in the sampling tube such that it cannot be affected by the chemicals, the transponder being arranged outside the absorption material.

2. A device according to claim 1,
   characterized in that the transponder is melted-in in a closed glass housing which constitutes an inseparable part of the device.

3. A device according to claim 1 characterized in that the transponder comprises an antenna.

4. A device according to claim 3,
   characterized in that the antenna is provided on the glass casing by a vapor deposition technique.

5. A device according to claim 4,
   characterized in that the vapor-deposited antenna is designed as a layer of metal ions vapor-deposited in a spiral path.

6. A device according to claim 3,
   characterized in that the antenna is designed as a coil-shaped element accommodated in the glass housing.

7. A device according to claim 1,
   characterized in that the memory of the transponder is programmable.

8. A device according to claim 7, characterized in that the memory of the transponder contains a non-erasable identification number.

9. The device according to claim 1 wherein the sampling tube is received in a package which is made of glass and filled with inert gas, the package having closed ends.

10. The device according to claim 1 wherein the absorption material is confined between two sieves.

11. The device according to claim 10 wherein the sieves are glass wool plugs.

12. The device according to claim 10 wherein the sieves are metal sieves.

13. The device according to claim 1 wherein the transponder is fixed between two sieves.

14. The device according to claim 13 wherein the sieves are glass wool plugs.

15. The device according to claim 13 wherein the sieves are metal sieves.

16. The device according to claim 1 wherein the transponder is fixed between two confined portions of the sampling tube.

* * * * *